(12) United States Patent
Wu et al.

(10) Patent No.: US 11,673,821 B2
(45) Date of Patent: Jun. 13, 2023

(54) METHOD OF FIXING ARSENIC USING ACTIVATED BIOCHAR (71) Applicant: Nanjing University, Jiangsu (CN)

(72) Inventors: Song Wu, Nanjing (CN); Dunfeng Si, Nanjing (CN); Dongmei Zhou, Nanjing (CN)

(73) Assignee: Nanjing University, Nanjing (CN)

( * ) Notice: Subject to any disclaimer, the term of this patent is extended or adjusted under 35 U.S.C. 154(b) by 0 days.

(21) Appl. No.: 17/387,862

(22) Filed: Jul. 28, 2021

(65) Prior Publication Data

US 2022/0340462 A1 Oct. 27, 2022

(30) Foreign Application Priority Data

Apr. 27, 2021 (CN) .......................... 202110460876.4

(51) Int. Cl.
*C02F 3/28* (2023.01)
*B01J 20/20* (2006.01)
*B01J 20/28* (2006.01)
*B01J 20/30* (2006.01)
*B09C 1/08* (2006.01)
*B09C 1/10* (2006.01)
*C02F 1/28* (2023.01)
*C10B 53/02* (2006.01)
*C12N 1/20* (2006.01)
*C02F 3/00* (2023.01)
*C02F 101/10* (2006.01)
*C02F 103/06* (2006.01)

(52) U.S. Cl.
CPC ............. *C02F 3/2813* (2013.01); *B01J 20/20* (2013.01); *B01J 20/28061* (2013.01); *B01J 20/28064* (2013.01); *B01J 20/28066* (2013.01); *B01J 20/3078* (2013.01); *B09C 1/08* (2013.01); *B09C 1/10* (2013.01); *C02F 1/283* (2013.01); *C10B 53/02* (2013.01); *C12N 1/20* (2013.01); *B01J 2220/4825* (2013.01); *C02F 2003/003* (2013.01); *C02F 2101/103* (2013.01); *C02F 2103/06* (2013.01)

(58) Field of Classification Search
CPC ......... C02F 3/2813; C02F 1/283; B01J 20/20; B01J 20/28061; B01J 20/28064; B01J 20/28066; B01J 20/3078; B09C 1/08; B09C 1/10; C10B 53/02; C12N 1/20
See application file for complete search history.

(56) References Cited

U.S. PATENT DOCUMENTS

2021/0122898 A1* 4/2021 Luthe ..................... C08J 11/00
2022/0097110 A1* 3/2022 Luthe ..................... B09B 5/00

* cited by examiner

*Primary Examiner* — Chester T Barry (57) ABSTRACT

The present disclosure provides a method of preparing a carbonaceous material capable of fixing arsenic and an application thereof. Through biomass pretreatment, biomass pyrolysis and arsenite fixation, a biochar activated by potassium carbonate and an arsenic-containing wastewater containing sulfur-containing substances are mixed and deoxidized, and an anaerobic culture is carried out, to fix arsenic by the biochar activated by potassium carbonate. The present disclosure solves the problems that arsenic is released from the soil and groundwater under anaerobic conditions, the ability of conventional passivating agents to fix arsenic under anaerobic conditions is weakened, and the conventional carbonaceous materials not only cannot fix arsenic, but also accelerate the release of anaerobic arsenic.

5 Claims, 7 Drawing Sheets

METHOD OF FIXING ARSENIC USING ACTIVATED BIOCHAR

CROSS-REFERENCE TO RELATED APPLICATION

This application claims priority from the Chinese patent application 202110460876.4 filed Apr. 27, 2021, the content of which is incorporated herein in the entirety by reference.

TECHNICAL FIELD

The present disclosure relates to the technical field of soil pollution and remediation, specifically relates to a method of preparing a carbonaceous material capable of fixing arsenic and an application thereof.

BACKGROUND

As a commonly-used environment remediation material, the carbonaceous material has broad application prospects in the remediation of soil organic and inorganic pollution. Because the surface of the carbonaceous material is usually negatively charged, a lot of research has applied it to the remediation of the pollution caused by cationic heavy metal pollutants ($Hg^{2+}$, $Cd^{2+}$, $Pb^{2+}$, $CU^{2+}$, $Zn^{2+}$, etc.). However, arsenic usually exists in the form of oxygen-containing anions ($AsO_4^{3-}$, $HAsO_4^{2-}$, $H_2AsO_4^-$, $AsO_3^{3-}$, $HAsO_3^{2-}$, $H_2AsO_3^-$) in the environment, and the adsorption capacity of the carbonaceous material to arsenic is very weak.

In the anaerobic soil and groundwater environments, the environment risk of arsenic is greatly increased with the reductive dissolution of arsenate. And since the carbonaceous material can promote the anaerobic release of arsenic due to its redox properties, it can further exacerbate the environmental risk of arsenic. Therefore, the carbonaceous material is usually modified to load iron-manganese oxide or titanium dioxide and other metal oxides having arsenic-adsorption capacity on its surface in the process of applying it to the soil, groundwater, and arsenic-containing wastewater treatment, making the carbonaceous material modified by metal oxides capable of efficiently adsorbing and fixing arsenic in the aerobic environment.

When the soil, groundwater, and arsenic-containing wastewater are converted from aerobic to anaerobic, the reductive dissolution of iron-manganese oxide in the metal oxide-loaded carbonaceous material can cause the partial release of arsenic, thereby reducing its fixation effect on arsenic. Therefore, it is necessary to develop a passivation material that can efficiently fix arsenite in the anaerobic environment, used for the remediation of the soil, groundwater, and arsenic-containing wastewater.

SUMMARY

In view of the problems in the prior art, the inventor of the present disclosure unexpectedly discovers that after mixing raw materials such as sawdust with potassium carbonate and the like for pyrolysis and other treatments, arsenite in the arsenic-containing wastewater can be fixed.

The object of the present disclosure is to provide a method of preparing a carbonaceous material capable of fixing arsenic, including biomass pretreatment, biomass pyrolysis, and arsenite fixation.

The above-mentioned solutions specifically comprise the following steps:

S1: biomass pretreatment a sawdust is used as a raw material to mix with potassium carbonate at a mass ratio of 1:1, and water is added for shaking culture for 4 h, to obtain a mixed solution, then the mixed solution is dried to obtain a mixture;

S2: biomass pyrolysis the mixture obtained in the S1 is added to a pyrolysis device for pyrolysis at the temperature of 500-900° C. for 2-3 h, and nitrogen is pumped as a protective gas during the pyrolysis, to obtain a biochar activated by potassium carbonate after the pyrolysis is completed;

S3: arsenite fixation a substance containing arsenite is dissolved, then sodium thiosulfate, *Shewanella oneidensis* MR-1 as an anaerobic microorganism and the biochar activated by potassium carbonate obtained in the S2 are added after the dissolution, and an anaerobic culture is carried out in a sealed environment by mechanical stirring for 4 h, to fix arsenite in the solution by the biochar activated by potassium carbonate.

Further, in the S3, the concentration of arsenite after dissolution is 7.5 $mgL^{-1}$, the concentration of sodium thiosulfate after addition is 2 $mmolL^{-1}$, and the addition amount of the biochar activated by potassium carbonate is 1 g/L. When dissolved sulfide ions are released, the biochar activated by potassium carbonate starts to fix arsenite.

Further, in the S3, *Shewanella oneidensis* MR-1 as the anaerobic microorganism is added in a form of bacterial liquid with the addition amount of 10 g/L and the concentration of 100 cFU/ml.

Further, the particle size of the sawdust in the S1 is 2000-3900 um. With a too-large particle size, the specific surface area of the sawdust can be reduced, thereby reducing the fixation effect on arsenite. The mechanical stirring in the S3 is carried out at the speed of 80-120 r/min for 10-15 min, and the temperature of the shaking culture is 30-40° C. A distillation method is used to dry the water in the solution, and the equilibrium moisture content of the sawdust after drying is 5-8%.

According to one aspect of the present disclosure, the raw material and potassium carbonate of the above-mentioned solutions are capable of being equivalently substituted, which is specified as follows:

The sawdust as the raw material in the step S1 is capable of being substituted by peanut stalk, soybean stalk or a mixture of peanut stalk and soybean stalk in any weight ratio. And when the raw material is peanut stalk, soybean stalk, or the mixture of peanut stalk and soybean stalk, the pyrolysis temperature is 600-800° C.;

potassium carbonate in the S1 is capable of being substituted by sodium hydroxide, potassium hydroxide, zinc chloride, or a mixture of sodium hydroxide and potassium hydroxide in any ratio.

According to one aspect of the present disclosure, the above-mentioned solutions can omit the biomass pretreatment of the S1, and directly carry out the biomass pyrolysis of the S2 to the raw material. The specific steps are as follows:

The sawdust in the step S1 is directly subjected to the biomass pyrolysis of the S2 with the pyrolysis temperature of 600-1000° C.; ammonia or carbon dioxide is used as an activation gas during the pyrolysis, to obtain a biochar activated by gas after the pyrolysis, which is also capable of efficiently fixing the arsenite Ammonia or carbon dioxide can promote the activation of the specific surface area of the biochar.

Another object of the present disclosure is to provide an application of the carbonaceous material capable of fixing arsenic for the treatment of the soil, groundwater, or arsenic-containing wastewater, which is specified as follows:

1) in an arsenic-containing wastewater containing sulfur-containing substances, after a biochar activated by potassium carbonate and the arsenic-containing wastewater containing sulfur-containing substances are mixed and deoxidized, and an anaerobic culture is carried out to generate sulfide ions in the mixed system, and then arsenic is fixed by the biochar activated by potassium carbonate. The biochar activated by potassium carbonate starts to fix arsenite through the generation of the sulfide ions; and 2) in an arsenic-containing wastewater containing sulfur-containing substances and no molybdate, the biochar activated by potassium carbonate is directly applied to the arsenic-containing wastewater containing sulfur-containing substances, and an anaerobic sludge is simultaneously inoculated for the anaerobic culture, and then arsenic is fixed by the biochar activated by potassium carbonate with the reduction of sulfate. Arsenic can be high-efficiently fixed through the reduction of sulfate, and the conditions for the anaerobic culture are constructed through the anaerobic sludge;

wherein, the sulfur-containing substances are composed of sulfate, sulfite, thiosulfate, elemental sulfur, or sulfide ions; and the biochar activated by potassium carbonate is capable of being equivalently substituted by the biochar activated by gas.

The beneficial effects of the present disclosure are as follows:

The present disclosure provides a method of preparing the carbonaceous material capable of fixing arsenic and an application thereof. By carrying out the direct pyrolysis of the raw material, and the pyrolysis after mixing the raw material with potassium carbonate or the pyrolysis of the raw material in a specific atmosphere, the prepared carbonaceous material with high specific surface area can efficiently fix dissolved arsenic in the soil and aqueous solution under the reduction of sulfate. At the same time, it solves the problems that arsenic is released from the soil and groundwater under anaerobic conditions, the ability of conventional passivatingagents to fix arsenic under anaerobic conditions is weakened, and the conventional carbonaceous materials not only cannot fix arsenic, but also accelerate the release of anaerobic arsenic. Therefore, the present disclosure has broad application prospects in the treatment of the soil, groundwater, and arsenic-containing wastewater.

DETAILED DESCRIPTION OF EMBODIMENTS

Unless otherwise specified, the materials and reagents used in the examples are all conventionally used in the art or commercially available.

Example 1

A method of preparing a carbonaceous material capable of fixing arsenic is provided, comprising the following steps:

S1: biomass pretreatment the sawdust with the particle size of 2400 um is used as the raw material, with too-large particle size, the specific surface area of the sawdust can be reduced to decrease the fixation effect on arsenite; the sawdust is mixed with potassium carbonate at the mass ratio of 1:1, and water is added for shaking culture for 4 h to obtain a mixed solution which is dried to obtain a mixture; the temperature for the shaking culture is 30° C.; a distillation method is used to dry the water in the solution, and the equilibrium moisture content of the sawdust after drying is 7%.

S2: biomass pyrolysis the mixture obtained in the S1 is added to a pyrolysis device for pyrolysis at the temperature of 800° C. for 2 h, and nitrogen is pumped as a protective gas during the pyrolysis, to obtain a biochar activated by potassium carbonate after the pyrolysis is completed;

S3: arsenite fixation a substance containing arsenite is dissolved, then sodium thiosulfate, the biochar activated by potassium carbonate, and *Shewanella oneidensis* MR-1 as an anaerobic microorganism are added after the dissolution, the concentration of arsenite after the dissolution of the substance containing arsenite is 7.5 $mgL^{-1}$, the concentration of sodium thiosulfate after addition is 2 $mmolL^{-1}$, and the addition amount of the biochar activated by potassium carbonate is 1 g/L; an anaerobic culture is carried out in a sealed environment for 4 h, by mechanical stirring at the speed of 100 r/m for 13 min for more fully stirring; when the dissolved sulfide ions are released, the biochar activated by potassium carbonate can fix arsenite in the solution; the concentration of *Shewanella oneidensis* MR-1 as the anaerobic microorganism is added in the form of bacterial liquid with the addition amount of 10 g/L and the concentration of 100 cFU/ml.

Meanwhile, an application of the carbonaceous material capable of fixing arsenic is provided for the treatment of the soil, groundwater, and arsenic-containing wastewater, which is specified as follows:

1) in the arsenic-containing wastewater containing sulfur-containing substances, after the biochar activated by potassium carbonate and the arsenic-containing wastewater containing sulfur-containing substances are mixed and deoxidized, the anaerobic culture is carried out to generate sulfide ions in the mixed system, and then arsenic is fixed by the biochar activated by potassium carbonate; the biochar activated by potassium carbonate starts to fix arsenite through the generation of the sulfide ions; and 2) in the arsenic-containing wastewater containing sulfur-containing substances and no molybdate, the biochar activated by potassium carbonate is directly applied to the arsenic-containing wastewater, and the anaerobic sludge is simultaneously inoculated for the anaerobic culture, and then arsenic is fixed by the biochar activated by potassium carbonate with the reduction of sulfate; arsenic can be high-efficiently fixed through the reduction of sulfate, and the conditions for the anaerobic culture are constructed through the anaerobic sludge;

wherein, the sulfur-containing substances are composed of sulfate, sulfite, thiosulfate, elemental sulfur, or sulfide ions.

Example 2

This example is basically the same as Example 1, and the difference is that the particle size of the sawdust in the S1 is specifically 2000 um.

Example 3

This example is basically the same as Example 1, and the difference is that the particle size of the sawdust in the S1 is specifically 3900 um.

Example 4

This example is basically the same as Example 1, and the difference is that the equilibrium moisture content of the sawdust after drying in the S1 is specifically 5%.

Example 5

This example is basically the same as Example 1, and the difference is that the equilibrium moisture content of the sawdust after drying in the S1 is specifically 8%.

Example 6

This example is basically the same as Example 1, and the difference is that the pyrolysis temperature in the S2 is specifically 500° C.

Example 7

This example is basically the same as Example 1, and the difference is that the pyrolysis temperature in the S2 is specifically 900° C.

Example 8

This example is basically the same as Example 1, and the difference is that the mechanical stirring in the S3 is carried out at the speed of 80 r/m for 13 min.

Example 9

This example is basically the same as Example 1, and the difference is that the mechanical stirring in the S3 is carried out at the speed of 120 r/m for 13 min.

Example 10

This example is basically the same as Example 1, and the difference is that the sawdust as the raw material in the S1 can be substituted by peanut stalk, and the pyrolysis temperature is 700° C. when the peanut stalk is used as the raw material.

Example 11

This example is basically the same as Example 1, and the difference is that the sawdust as the raw material in the S1 can be substituted by soybean stalk, and the pyrolysis temperature is 700° C. when the soybean stalk is used as the raw material.

Example 12

This example is basically the same as Example 1, and the difference is that potassium carbonate in the S1 can be substituted by sodium hydroxide.

Example 13

This example is basically the same as Example 1, and the difference is that potassium carbonate in the S1 can be substituted by potassium hydroxide.

Example 14

This example is basically the same as Example 1, and the difference is that the biochar activated by potassium carbonate can be equivalently substituted by the biochar activated by gas; the steps of preparing the biochar activated by gas are as follows: the sawdust in the step S1 is directly subjected to the biomass pyrolysis of the S2 with the pyrolysis temperature of 800° C., and ammonia or carbon dioxide is used as an activation gas during the pyrolysis, to obtain the biochar activated by gas after the pyrolysis, which is also capable of efficiently fixing arsenite. And ammonia or carbon dioxide can promote the activation of the specific surface area of the biochar.

Example 15

This example is basically the same as Example 12, and the difference is that the pyrolysis temperature is specifically 600° C.

Example 16

This example is basically the same as Example 12, and the difference is that the pyrolysis temperature is specifically 1000° C.

Experimental Example

Figure 1:
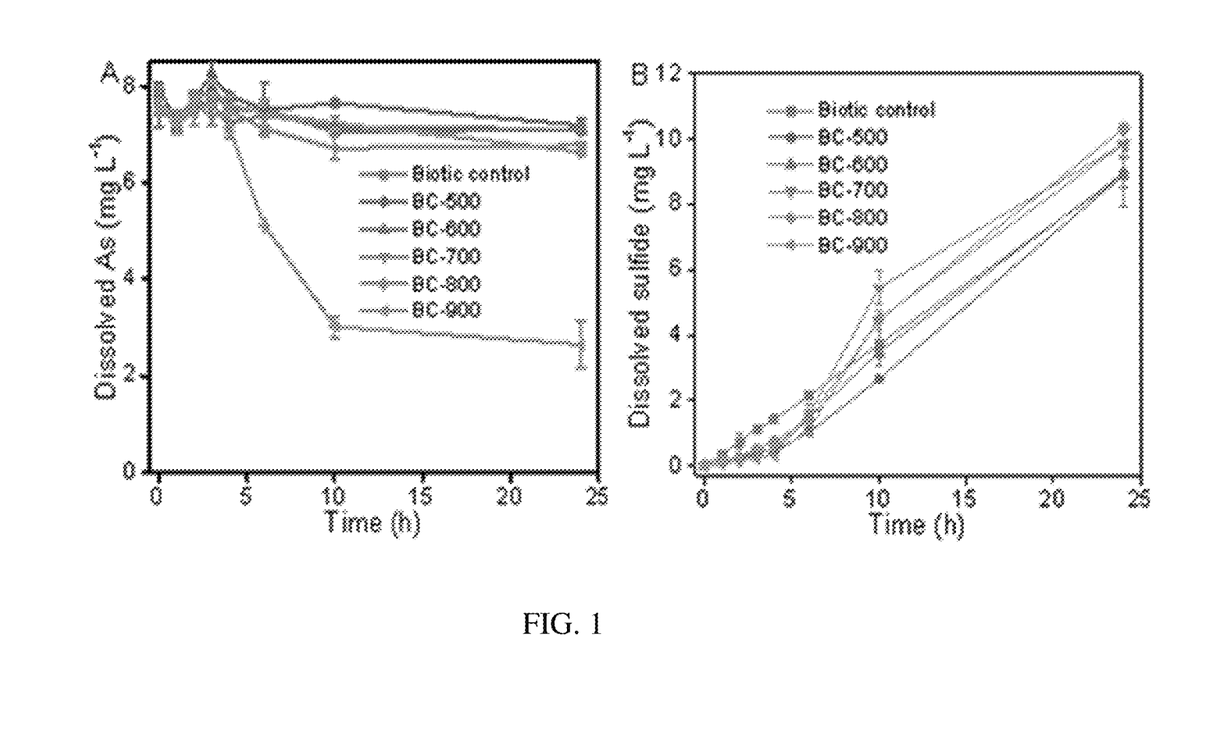
FIG. 1 is the fixation effect of a biochar prepared by a sawdust at the pyrolysis temperature of 500-900° C. for 2 h on arsenic under anaerobic conditions (A) and the release amount of sulfide ions in a system (B).

Experiment 1 To explore the effect of different pyrolysis temperatures, direct pyrolysis, and pretreatment on the performance of biochar 1) The biomass is pyrolyzed at a high temperature of 500-900° C., corresponding to Examples 1, 6 and 7. The sawdust is used as the raw material, the pyrolysis temperature is controlled at 500, 600, 700, 800 and 900° C. respectively, and the pyrolysis is carried out for 2 h to prepare the biochar, named BC-500~BC-900 respectively. The anaerobic culture system is constructed by 1 gL$^{-1}$ of the biochar, 7.5 mgL$^{-1}$ of the dissolved arsenite, 2 mmolL$^{-1}$ of sodium thiosulfate and *Shewanella oneidensis* MR-1 as the anaerobic microorganism for the anaerobic culture, and the content of the dissolved arsenic and sulfide ions is monitored. As shown in FIG. 1, all biochar can not fix arsenic during the first 4 h of the culture due to the absence of sulfide ions; when the dissolved sulfide ions are released, BC-500~BC-800 still cannot fix arsenic, but BC-900 can fix arsenic.

Figure 2:
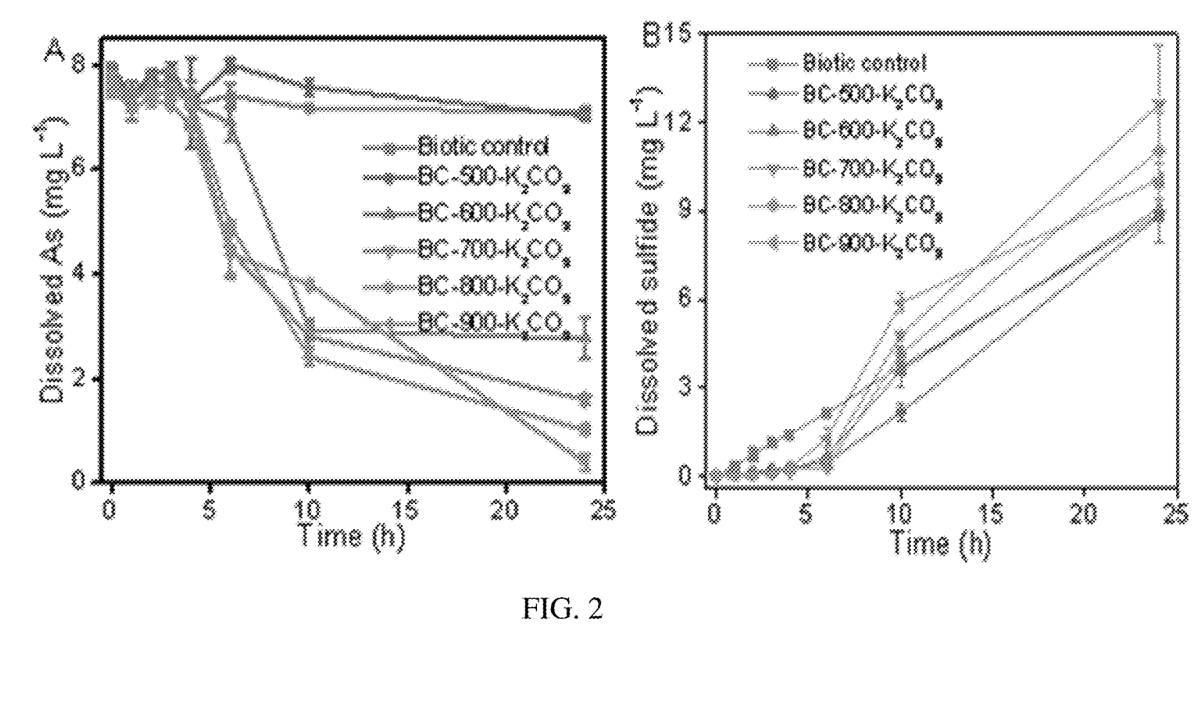
FIG. 2 is the fixation effect of a biochar prepared by a mixture of the sawdust and potassium carbonate at the pyrolysis temperature of 500-900° C. for 2 h on arsenic under the anaerobic conditions (A) and the release amount of the sulfide ions in the system (B).

2) The biomass is pyrolyzed at a high temperature of 500-900° C. and mixed with potassium carbonate, and the pyrolysis is carried out at a high temperature of 500-900° C., corresponding to Examples 14, 15 and 16. The sawdust is used as the raw material to mix with potassium carbonate at a mass ratio of 1:1, and water is added for shaking culture for 4 h, and then the mixture is dried. The pyrolysis temperature is controlled at 500, 600, 700, 800 and 900° C. respectively, and the mixture of the biomass and potassium carbonate is pyrolyzed for 2 h to prepare the biochar activated by potassium carbonate, named BC-500-K$_2$CO$_3$~BC-900-K$_2$CO$_3$. The anaerobic culture system is constructed by 7.5 mgL$^{-1}$ of the dissolved arsenite, 2 mmol/L of sodium thiosulfate and *Shewanella oneidensis* MR-1 as the anaerobic microorganism for the anaerobic culture, and the content of the dissolved arsenic and sulfide ions is monitored. The comparison of the results of FIG. 1 with FIG. 2 shows that when the pyrolysis temperature is greater than 500° C., potassium carbonate can efficiently activate the sawdust biomass, making it from unable to fix arsenic to being able to fix arsenic.

At the same time, the main element composition and specific surface area values of the sawdust biochar and the sawdust biochar activated by potassium carbonate at different pyrolysis temperatures are shown in Table 1.

| Biochar | Element composition | | | | BET (m$^2$g$^{-1}$) |
|---|---|---|---|---|---|
| | N % | C % | H % | S % | |
| BC-500 | 0.41 | 83.04 | 4.153 | 0 | |
| BC-600 | 0.36 | 86.16 | 3.452 | 0.046 | 479 |
| BC-700 | 0.33 | 89.34 | 2.862 | 0.066 | 452 |
| BC-800 | 0.36 | 90.32 | 2.429 | 0.092 | 457 |
| BC-900 | 0.32 | 88.85 | 2.293 | 0.115 | 638 |
| BC-500-K$_2$CO$_3$ | 0.18 | 86.03 | 3.329 | 0.078 | |
| BC-600-K$_2$CO$_3$ | 0.18 | 70.26 | 3.07 | 0.105 | 582 |
| BC-700-K$_2$CO$_3$ | 0.47 | 86.98 | 2.248 | 0.143 | 1596 |
| BC-800-K$_2$CO$_3$ | 0.49 | 85.75 | 3.329 | 0.179 | 1238 |
| BC-900-K$_2$CO$_3$ | 0.29 | 75.88 | 2.705 | 0.134 | 1328 |

Experimental Conclusion

The fixation effect of the biochar prepared by the sawdust at the pyrolysis temperature of 500-900° C. for 2 h on arsenic under anaerobic conditions (A) and the release amount of sulfide ions in the system (B), and the system composition: 1 gL$^{-1}$ of the biochar, 7.5 mgL$^{-1}$ of arsenite, 2 mmol/L of sodiumthiosulfate, and *Shewanella oneidensis* MR-1 as the anaerobic microorganism are shown in FIG. 1.

The fixation effect of the biochar prepared by the mixture of the sawdust and potassium carbonate at the pyrolysis temperature of 500-900° C. for 2 h on arsenic under the anaerobic conditions (A) and the release amount of the sulfide ions in the system (B), and the system composition: 7.5 mgL$^{-1}$ of arsenite, 2 mmol/L of sodiumthiosulfate, and *Shewanella oneidensis* MR-1 as the anaerobic microorganism are shown in FIG. 2.

Figure 3:
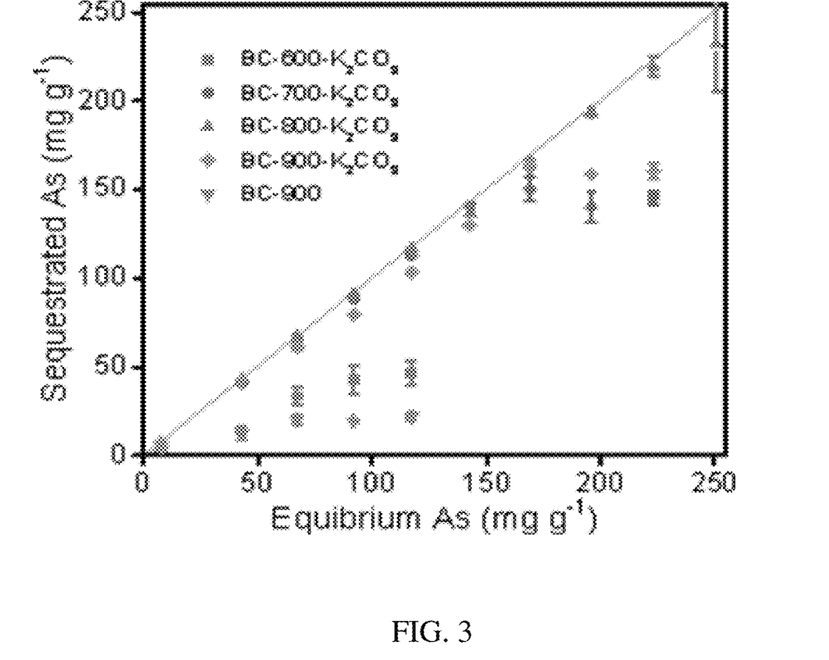
FIG. 3 is the capacity of a sawdust biochar activated by potassium carbonate (BC-600-$K_2CO_3$~BC-900-$K_2CO_3$) and a sawdust biochar (BC-900) prepared at 900° C. to fix arsenic under the anaerobic conditions.

As shown in FIG. 3, with the increase of the pyrolysis temperature, the capability of the biochar activated by potassium carbonate to fix arsenic gradually increases. The capacity of BC-800-K$_2$CO$_3$ to fix arsenic is the highest, reaching 232 mgg$^{-1}$. When the temperature is further increased to 900° C., the capacity of BC-800-K$_2$CO$_3$ to fix arsenic is reduced, but it is still much higher than that of BC-900.

The capacity of the sawdust biochar activated by potassium carbonate (BC-600-K$_2$CO$_3$~BC-900-K$_2$CO$_3$) and the sawdust biochar prepared at 900° C. (BC-900) to fix arsenic under the anaerobic conditions are shown in FIG. 3.

Figure 4:
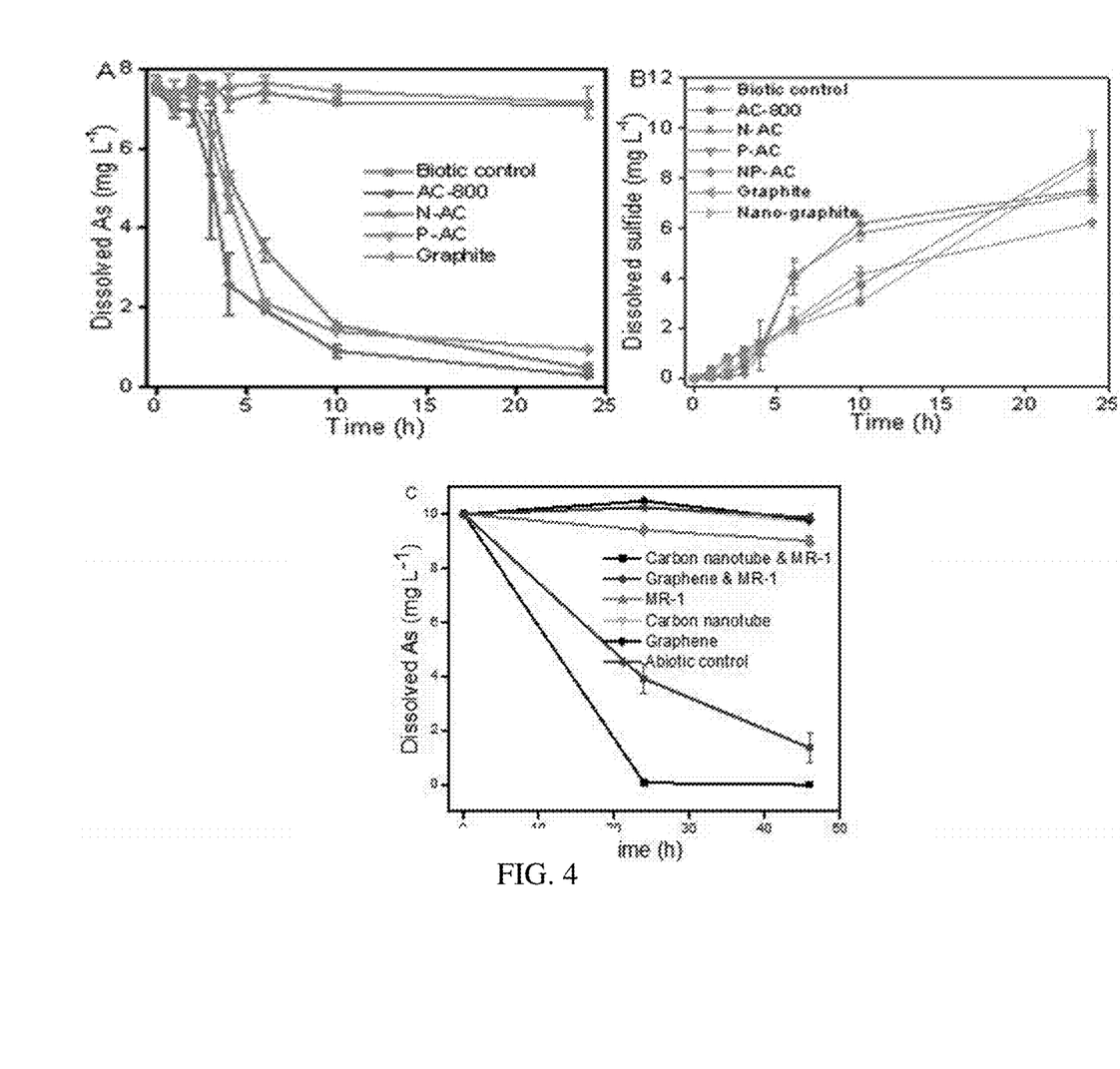
FIG. 4 is the fixation effect of different types of activated carbon (activated carbon prepared at 800° C., AC-800; nitrogen-doped activated carbon, N-AC; and phosphorus-doped activated carbon, P-AC) and graphite, as well as carbon nanotube and graphene on arsenic under the anaerobic conditions (A, C) and the release amount of the sulfide ions in the system (B).
Figure 5:
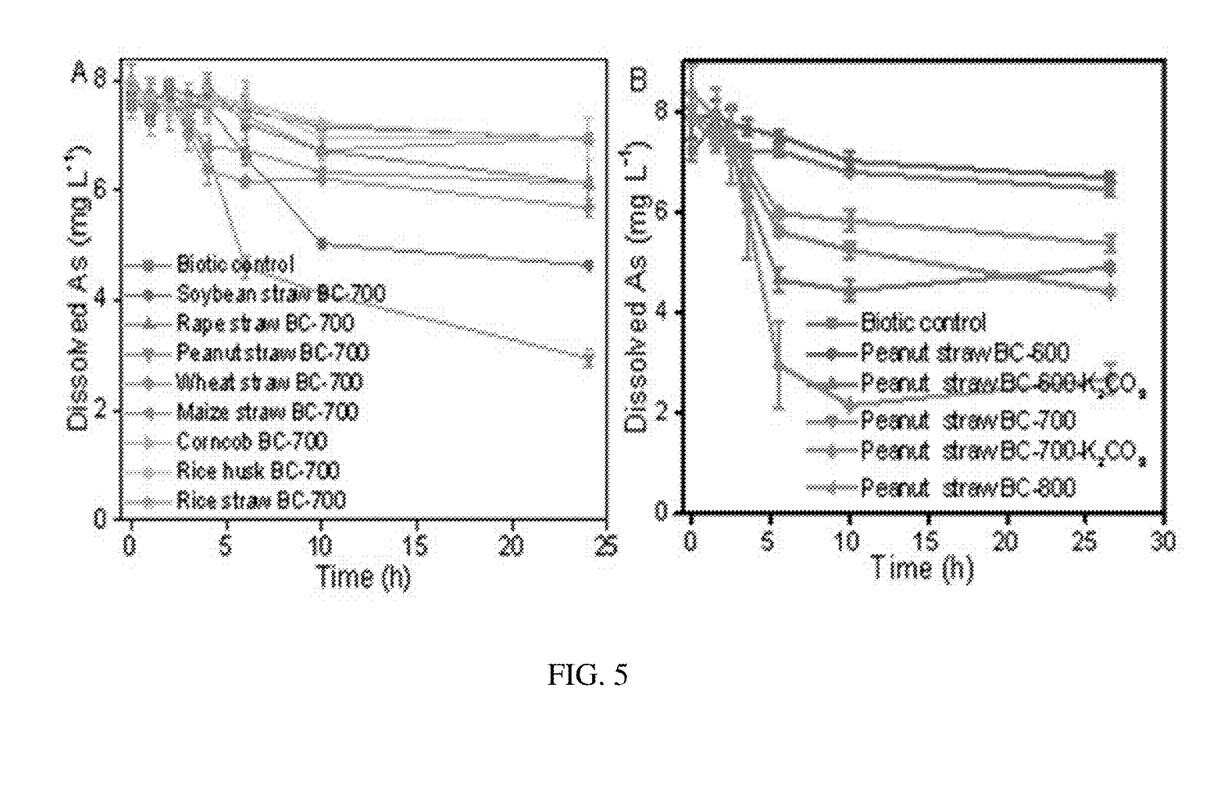
FIG. 5 is the fixation effect of a biochar prepared by different types of biomasses for pyrolysis at 700° C. for 2 h (A), and a biochar prepared by peanut stalk at 600-800° C. and a peanut stalk charcoal activated by potassium carbonate (peanut stalk:potassium carbonate=2:1, B) on arsenic under the anaerobic conditions.

Experiment 2 To explore the fixation effect of different types of activated carbon, graphite, graphene, and carbon nanotube on arsenic under the anaerobic conditions As shown in FIG. 4, the different types of commercial activated carbon are selected for experiments, and it is found that activated carbon, graphene, and carbon nanotube with larger specific surface area can fix arsenic, while graphite with high conductivity and small specific surface area cannot fix arsenic. It further demonstrates that the specific surface area of the biochar plays a decisive role in the fixation of arsenic.

FIG. 4 is the fixation effect of different types of activated carbon (activated carbon prepared at 800° C., AC-800; nitrogen-doped activated carbon, N-AC; and phosphorus-doped activated carbon, P-AC) and graphite, as well as carbon nanotube and graphene on arsenic under the anaerobic conditions (A, C) and the release amount of the sulfide ions in the system (B), and the system composition: 7.5 mgL$^{-1}$ of arsenite, 2 mmol/L of sodiumthiosulfateand, and *Shewanella oneidensis* MR-1 as the anaerobic microorganism.

Experiment 3 To explore the effect of different biomass raw materials on the performance of the biochar The specific types of biomasses are selected to pyrolyze at 500-1000° C., corresponding to Examples 10 and 11. Soybean stalk, rape stalk, peanut stalk, wheat stalk, corn stalk, corn cob, rice husk, and rice stalk are selected to prepare the biochar by pyrolyzing at 700° C. for 2 h.

Experimental conclusion: As shown in FIG. 4, peanut stalk and soybean stalk can efficiently fix arsenic, while the capability of other stalks to fix arsenic is very weak; then peanut stalk is selected to prepare the biochar at 600-800° C. or the biochar activated by potassium carbonate: the biochar prepared at 700° C. and 800° C. under direct pyrolysis conditions can effectively fix arsenic; the biochar prepared at 600° C. under potassium carbonate activation conditions can fix arsenic.

The fixation effect of the biochar prepared by different types of biomass for pyrolysis at 700° C. for 2 h (A), and the biochar prepared by peanut stalk at 600-800° C. and the peanut stalk charcoal activated by potassium carbonate (peanut stalk:potassium carbonate=2:1, B) on arsenic under the anaerobic conditions, and the system composition: 7.5 mgL$^{-1}$ of arsenite, 2 mmol/L of sodiumthiosulfateand, and *Shewanella oneidensis* MR-1 as the anaerobic microorganism are shown in FIG. 4.

Experiment 4 To explore the effect of different particle sizes of the sawdust on the performance of the biochar This experiment corresponds to Examples 1, 2 and 3. According to the results of Experiment 1, the fixation effect of the biochar activated by potassium carbonate at the pyrolysis temperature of 800° C. on arsenite in Example 1 is decreased from 8 mgL$^{-1}$ to 1.4 mgL$^{-1}$ after 20 h.

However, the fixation effect of the biochar activated by potassium carbonate at the pyrolysis temperature of 800° C. on arsenite in Example 2 is decreased from 8 mgL$^{-1}$ to 1.4 mgL$^{-1}$ after 20 h.

The fixation effect of the biochar activated by potassium carbonate at the pyrolysis temperature of 800° C. on arsenite in Example 3 is decreased from 8 mgL$^{-1}$ to 1.9 mgL$^{-1}$ after 20 h.

Experimental conclusion: the particle size of the sawdust used in Example 2 is 2000 um, and the particle size of the sawdust used in Example 1 is 2400 um. However, there is almost no influence on the fixation effect of the prepared biochar activated by potassium carbonate on arsenite. The particle size of the sawdust used in Example 3 is 3900 um. The fixation effect of the prepared biochar activated by potassium carbonate on arsenite is significantly decreased compared to that in Example 1. Therefore, from the fixation effect on arsenite and the economic point of view, the particle size of the sawdust used in Example 1 is more suitable.

Experiment 5 To explore the effect of different equilibrium moisture contents of the sawdust on the performance of the biochar This experiment corresponds to Examples 1, 4 and 5. According to the results of Experiment 1, the fixation effect of the biochar activated by potassium carbonate on arsenite in Example 1 is decreased from 8 mgL$^{-1}$ to 1.4 mgL$^{-1}$ after 20 h.

However, the fixation effect of the biochar activated by potassium carbonate on arsenite in Example 4 is decreased from 8 mgL$^{-1}$ to 1.6 mgL$^{-1}$ after 20 h.

The fixation effect of the biochar activated by potassium carbonate on arsenite in Example 5 is decreased from 8 mgL$^{-1}$ to 1.5 mgL$^{-1}$ after 20 h.

Experimental conclusion: the drying degrees of the sawdust used in Examples 4 and 5 are different from that in Example 1, and the use effect of the prepared biochar activated by potassium carbonate is also different, but it has little influence on the fixation effect of arsenite. The biochar activated by potassium carbonate prepared in Example 1 that the equilibrium moisture content of the sawdust after drying is 7% has a relatively better fixation effect on arsenite.

Experiment 6 To explore the effect of different mechanical stirring parameters on the performance of the biochar This experiment corresponds to Examples 1, 8 and 9. According to the results of Experiment 1, the fixation effect of the biochar activated by potassium carbonate on arsenite in Example 1 is decreased from 8 mgL$^{-1}$ to 1.4 mgL$^{-1}$ after 20 h.

However, the fixation effect of the biochar activated by potassium carbonate on arsenite in Example 8 is decreased from 8 mgL$^{-1}$ to 1.7 mgL$^{-1}$ after 20 h.

The fixation effect of the biochar activated by potassium carbonate on arsenite in Example 9 is decreased from 8 mgL$^{-1}$ to 1.3 mgL$^{-1}$ after 20 h.

Experimental conclusion: the mechanical stirring parameters used in Examples 8 and 9 are different from that in Example 1, and the rotation speed in Example 9 is faster than that in Example 1, but the fixation effect on arsenite is less improved. The rotation speed in Example 8 is slower than that in Example 1, and the fixation effect on arsenite is significantly reduced. Therefore, from the perspective of the fixation effect on arsenite and economic point of view, the power consumption of the mechanical stirring in Example 1 is lower than that in Example 9, and the fixation effect is also better.

Experiment 7 To explore the effect of the use of potassium carbonate, sodium hydroxide or potassium hydroxide on the performance of the biochar This experiment corresponds to Examples 1, 12 and 13. According to the results of Experiment 1, the fixation effect of the biochar activated by potassium carbonate on arsenite in Example 1 is decreased from 8 mgL$^{-1}$ to 1.4 mgL$^{-1}$ after 20 h.

However, the fixation effect of the biochar activated by potassium carbonate on arsenite in Example 12 is decreased from 8 mgL$^{-1}$ to 1.6 mgL$^{-1}$ after 20 h.

The fixation effect of the biochar activated by potassium carbonate on arsenite in Example 13 is decreased from 8 mgL$^{-1}$ to 1.7 mgL$^{-1}$ after 20 h.

Experimental conclusion: Example 12 uses sodium hydroxide to substitute potassium carbonate in Example 1, and its fixation effect on arsenite is reduced to a certain extent compared with that of the biochar activated by potassium carbonate in Example 1, but its fixation effect on arsenite is still better. Example 13 uses potassium hydroxide to substitute potassium carbonate in Example 1, and its fixation effect on arsenite is reduced to a certain extent compared with that of the biochar activated by potassium carbonate in Example 1, as well as its use effect is relatively worse than that of sodium hydroxide, but its fixation effect on arsenite is still better.

Application Example

Application 1: The biochar activated by potassium carbonate, and the arsenic-containing wastewater containing sulfur-containing substances (including sulfite, thiosulfate, elemental sulfur, or sulfide ions, etc.) are mixed and deoxidized, and then cultured under the anaerobic conditions to generate sulfide ions in the mixed system, and then the biochar activated by potassium carbonate can fix arsenic.

As shown in FIGS. 1-5, the anaerobic culture system constructed by the dissolved arsenite, sodium thiosulfate and *Shewanella oneidensis* MR-1 as the anaerobic microorganism demonstrates that the biochar of the present disclosure can high-effectively fix arsenic in a reduction environment that the sulfide ions are generated.

Application 2: The biochar is directly applied to the arsenic-contaminated soil or arsenic-containing wastewater, and cultured under the anaerobic conditions, so that the system forms a sulfate reduction environment, to high-effectively fix arsenic.

When the anaerobic sludge is inoculated in the arsenic-containing wastewater for the anaerobic culture: in the wastewater containing sulfate, arsenic can be high-effectively fixed with the reduction of sulfate; in the wastewater containing no sulfate, arsenic cannot be fixed; in the wastewater containing both sulfate and molybdate, since molybdate inhibits the reduction of sulfate by microorganisms, arsenic cannot be fixed.

Figure 6:
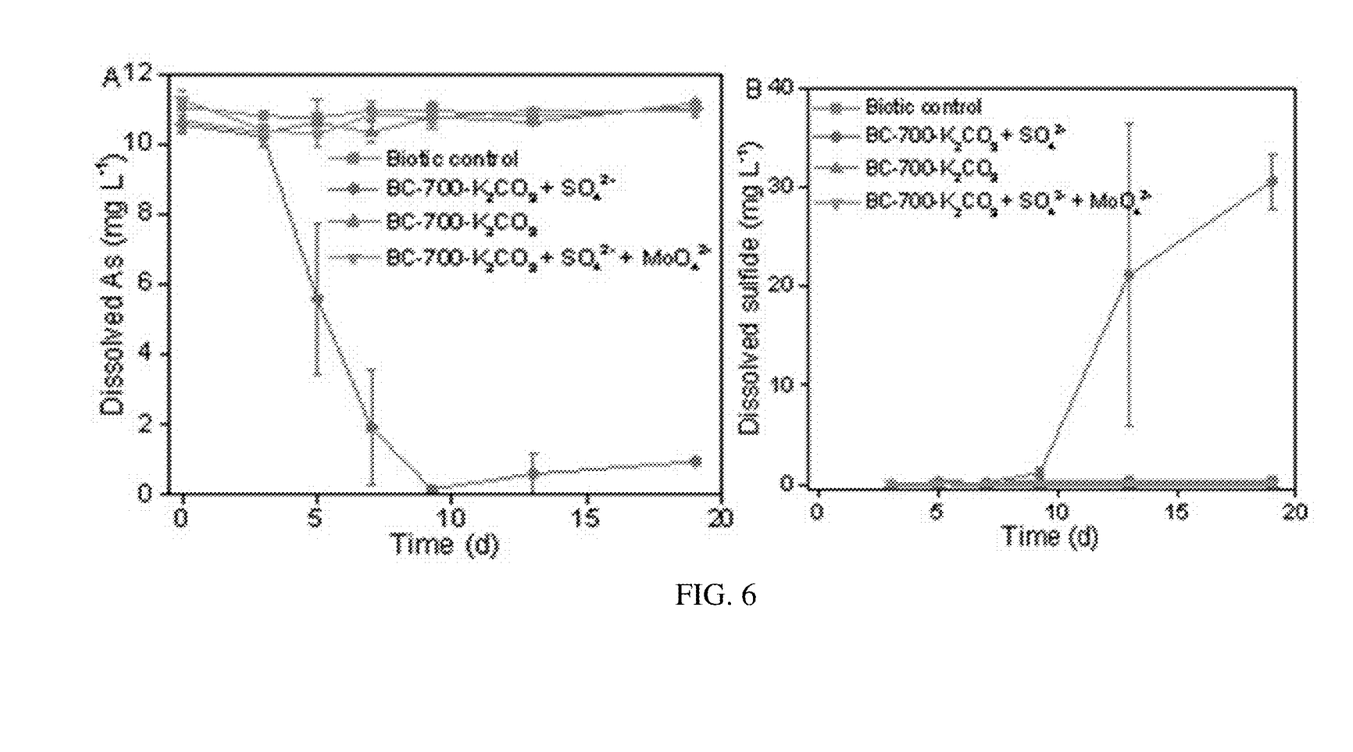
FIG. 6 is the removal of arsenite from an arsenic-containing wastewater containing sulfate, no sulfate, and both sulfate and molybdate (sulfate reduction inhibitor) by a biochar activated by potassium carbonate (BC-700-$K_2CO_3$) (A) and the release amount of the sulfide ions (B).

FIG. 6 shows the removal of arsenite in the arsenic-containing wastewater containing sulfate, no sulfate, and both sulfate and molybdate (sulfate reduction inhibitor) by the biochar activated by potassium carbonate (BC-700-$K_2CO_3$) (A) and the release of sulfide ions (B).

When the activated carbon with high specific surface area (AC) and the biochar prepared at 500° C. (BC-500) are mixed into the arsenic-contaminated soil at a ratio of 1% respectively, and the obtained mixture is added into a serum bottle with the soil-to-water ratio of 1:2 for the anaerobic culture, the activated carbon with high specific surface area can efficiently inhibit the anaerobic release of arsenic in the soil with the increase of the culture time, compared with the control soil and the experimental group added with the biochar prepared at 500° C.

Figure 7:
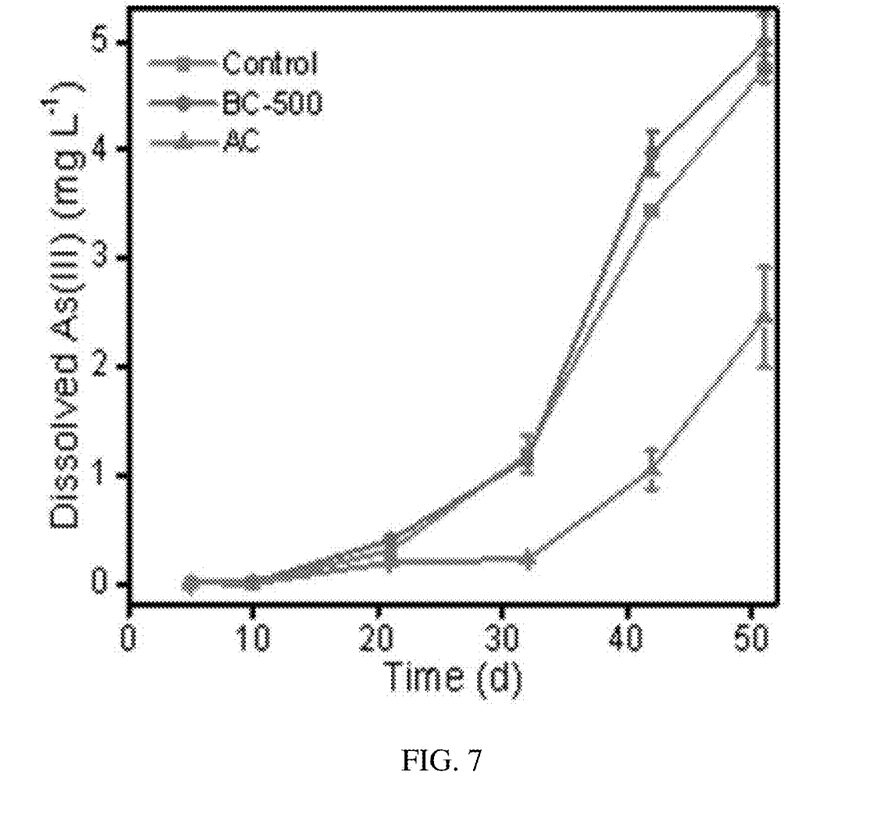
FIG. 7 is the inhibitory effect of an activated carbon with high specific surface area (AC) and a biochar prepared at 500° C. (BC-500) on the anaerobic release of arsenic in the arsenic-contaminated soil.

As shown in FIG. 7, the activated carbon with high specific surface area (AC) and the biochar prepared at 500° C. (BC-500) can inhibit the anaerobic release of arsenic in the arsenic-contaminated soil.

What is claimed is:

1. A method of fixing arsenic, wherein, the method comprises the following steps:
   S1: biomass pretreatment
   (a) mixing sawdust with potassium carbonate at a mass ratio of 1:1 to form a solids mixture,
   (b) adding water to the solids mixture to form an aqueous mixture,
   (c) shaking the aqueous mixture for 4 h to obtain a shaken mixture,
   (d) drying the shaken mixture to obtain a dried mixture;
   S2: biomass pyrolysis
   (a) adding the dried mixture to a pyrolysis device,
   (b) pyrolyzing the dried mixture at a temperature of 500-900° C. for 2-3 h under a nitrogen gas atmosphere pumped into the pyrolysis device during the pyrolysis to obtain a potassium carbonate-activated biochar;
   S3: arsenite fixation
   (a) first dissolving a substance comprising arsenite in water to form an arsenite solution, then
   (b) adding sodium thiosulfate, *Shewanella oneidensis* MR-1 microorganism and the potassium carbonate-activated biochar to the arsenite solution, and
   (c) anaerobically culturing the added microorganism in a sealed environment for 4 h with mechanical stirring to fix the arsenite to the potassium carbonate-activated biochar.

2. The method of fixing arsenic according to claim 1, wherein upon completion of step S3(b), the concentration of arsenite is 7.5 mg/L, the concentration of sodium thiosulfate is 2 mmol/L, and the concentration of potassium carbonate-activated biochar is 1 g/L.

3. The method of fixing arsenic according to claim 1, wherein the microorganism is added in the form of a 100 CFU/ml bacterial liquid which, upon completion of step S3(b), is present at a concentration of 10 g/L.

4. The method of fixing arsenic according to claim 1, wherein, the particle size of the sawdust of step S1(a) is 2000-3900 μm; the mechanical stirring of step S3(c) includes stirring for 10-15 min at 80-120 RPM, and the shaking of step S1(c) takes place at a temperature of 30-40° C.

5. A method of fixing arsenic, the method comprising:
   S1: biomass pretreatment
   (a) mixing a raw material with a compound at a mass ratio of 1:1,
   (b) adding water to the mixed composition resulting from step S1 (a) to form an aqueous mixture,
   (c) shaking the aqueous mixture for 4 h to obtain a shaken mixture, and
   (d) drying the shaken mixture to obtain a dried mixture;
   S2: biomass pyrolysis
   (a) adding the dried mixture to a pyrolysis device,
   (b) pyrolyzing the dried mixture at a temperature of 500-900° C. for 2-3 h under a nitrogen gas atmosphere pumped into the pyrolysis device during the pyrolysis to obtain a biochar activated by the compound;
   S3: arsenite fixation
   (a) first dissolving a substance comprising arsenite in an arsenite solution, then
   (b) adding sodium thiosulfate, *Shewanella oneidensis* MR-1 microorganism and the activated biochar of step S2 to the arsenite solution, and
   (c) anaerobically culturing the added microorganism in a sealed environment for 4 h with mechanical stirring to fix the arsenite to the compound-activated biochar;
   wherein the raw material comprises peanut stalk and/or soybean stalk; and
   the compound comprises zinc chloride or comprises sodium hydroxide and/or potassium hydroxide.

* * * * *